June 10, 1958 D. R. VESTAL Plant Pat. 1,716

PEACH TREE

Filed June 24, 1957

WITNESS

Addison E. Avery

INVENTOR

Dareld R. Vestal

Webster & Webster

ATTYS.

United States Patent Office

Plant Pat. 1,716
Patented June 10, 1958

1,716

PEACH TREE

Dareld R. Vestal, Red Bluff, Calif., assignor to Reedley Nursery, Inc., Reedley, Calif., a corporation Application June 24, 1957, Serial No. 667,730

1 Claim. (Cl. 47—62)

This discovery relates to a new and distinct variety of peach tree which originated as a bud sport of a Redhaven peach, and—while having general resemblance thereto—is primarily characterized, as to novelty, by large, yellow fleshed, freestone fruit having a ripening period approximately two weeks earlier than such Redhaven peach.

The present variety is further characterized by blooming—on the average—three to four days in advance of the Redhaven peach.

The instant variety of peach tree was discovered by me in June 1954—as I was checking for peach maturity—growing as a scaffold limb on a Redhaven peach tree in a commercial orchard on my ranch located near Red Bluff, California. When discovered, the fruit on such limb was very red and firm ripe, while the fruit on the remainder of the tree was still green and hard.

Subsequent and continuing observations by me of the mutation confirmed my original discovery, and I thereafter asexually propagated the variety by budding on mature Redhaven peach trees and a Hales Early peach tree growing on the aforesaid ranch.

All of these asexual reproductions have now come into bearing and by close comparison are found to carry forward all of the characteristics of the parent mutation.

Figure 1:
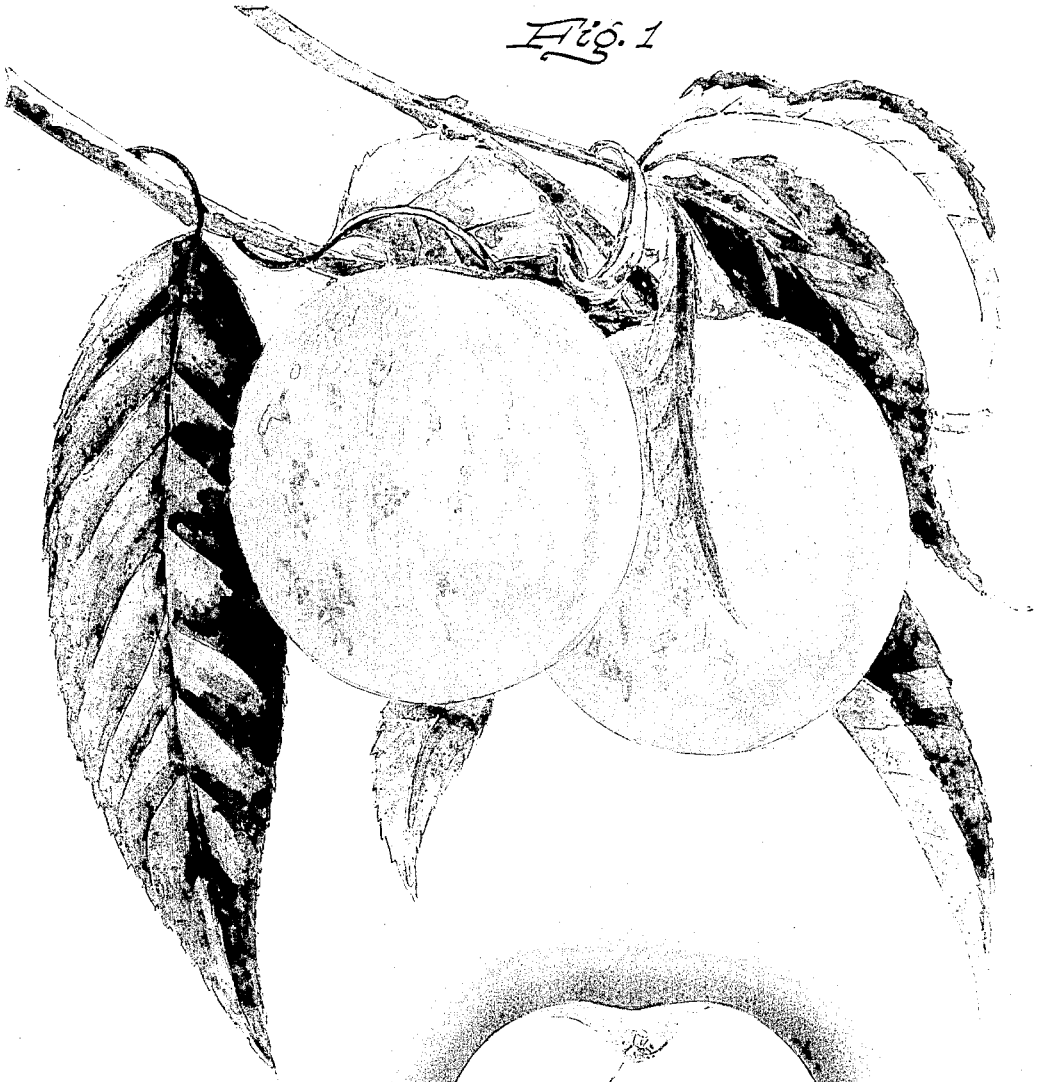
Fig. 1 is an elevation showing twigs, leaves, and two fruit of the variety.
Figure 2:
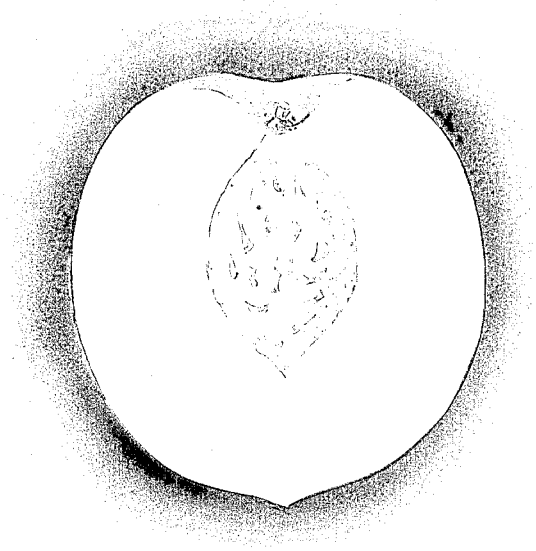
Fig. 2 is a sectional elevation of the fruit, with the stone exposed.

Referring now more specifically to the pomological details of this new and distinct variety of peach tree, the following is an outline description thereof; all major color plate identifications being by reference to Maerz and Paul Dictionary of Color:

Tree:
- *Size.*—Medium.
- *Vigor.*—Medium.
- *Growth.*—Normal—average.
- *Shape.*—Usually vase formed; controlled by pruning.
- *Production.*—Productive.
- *Bearing.*—Regular bearer.

Trunk:
- *Size.*—Medium stocky.
- *Texture.*—Medium shaggy.

Branches:
- *Size.*—Medium stocky.
- *Texture.*—Medium shaggy.
- *Color.*—Reddish brown on new wood—grey on older wood.
- *Lenticels.*—Medium number; medium to large size.

Leaves:
- *Size.*—Large. Average length—6" to 6½". Average width—1⅛" to 1½".
- *Form.*—Lanceolate; tip acuminate.
- *Thickness.*—Medium.
- *Texture.*—Smooth; rugose along midrib.
- *Margin.*—Finely serrate.

- *Petiole.*—Medium length; medium slender.
- *Glands.*—Average number—none to seven. Opposite; medium size; reniform; green, sometimes showing a little red; usually positioned on petiole and lower edge of leaf.
- *Stipules.*—Alongside the new leaves, falling off early.
- *Color.*—Top side—medium green (22–L–7). Under side—lighter green (21–K–5).

Flower buds:
- *Size.*—Medium.
- *Length.*—Medium.
- *Form.*—Round; plump; free; pubescent.

Flowers:
- *Blooming period.*—Date of first bloom—March 8, 1957. Date of full bloom—March 20, 1957. Medium in season, about three to four days earlier than Redhaven peach.
- *Pollen.*—Abundant.
- *Anthers.*—Reddish-orange before opening.
- *Size.*—Small.
- *Color.*—Pink, with edges darker than center of petal.

Fruit:
- *Maturity when described.*—Firm ripe, few eating ripe, June 16, 1957.
- *Size.*—Fairly uniform; medium. Average diameter axially—2⅜" to 2¾". Transversely in suture plane—2¼" to 2½". At right angles to suture plane—2¼" to 2½".
- *Form.*—Ovoid to sometimes nearly round or globose.
- *Suture.*—Distinct; shallow; extends from base to beyond, but discontinues at apex; slight depression beyond pistil point.
- *Ventral surface.*—Slightly rounded throughout; lips usually unequal.
- *Cavity.*—Slightly elongated, with suture showing on both sides. Average depth—¼" to ½". Average breadth—½" to ¾". Markings—none except where blush extends into cavity.
- *Base.*—Retuse.
- *Apex.*—Short; mucronate.
- *Pistil point.*—Apical.

Skin:
- *Thickness.*—Medium.
- *Texture.*—Medium tough; tenacious to flesh, except when very soft ripe.
- *Tendency to crack.*—None.
- *Down.*—Some, but scant and short.
- *Color.*—Yellow (10–J–5 to 10–K–8), ½ to ¾ of surface having a red blush (4–A–12 to 4–L–12), with some mottling (4–C–11 to 7–L–6).

Flesh:
- *Amygdalin.*—Moderate.
- *Texture.*—Firm; meaty.
- *Fibers.*—Few; tender.
- *Ripens.*—Evenly.
- *Flavor.*—Sub-acid; vinous.
- *Aroma.*—Distinct.
- *Eating quality.*—Good to best.
- *Color.*—Yellow (9–J–4 to 9–K–5), with some green near pit when firm ripe. Surface of pit cavity—yellow.

Stone:
- *Type.*—Semi-free to free; i. e. semi-free when firm ripe, and free when soft ripe. Adheres to flesh when firm ripe on both dorsal and ventral edges close to stem end.
- *Size.*—Medium. Average length—1½" to 1¾". Average breadth—1½" to 1⅛". Average thickness—¾" to ⅞".
- *Form.*—Obovate.
- *Base.*—Straight.
- *Hilum.*—Oval.

*Apex.*—Acuminate.
*Sides.*—Unequal; flattened on left side.
*Surface.*—Irregularly furrowed near base and toward apex, pitted throughout.
*Ridges.*—Jagged toward apex; interrupted.
*Pits.*—Usually circular.
*Ventral edge.*—Thick, with wing toward base.
*Dorsal edge.*—Deep groove toward base.
*Tendency to split.*—Slight.
*Color.*—Light tan (9–E–4).

Use: Market; local; dessert; culinary.
Keeping quality: Good.
Shipping quality: Good The previously existing varieties of peach trees, heretofore mentioned in this specification, are unpatented.

The tree and its fruit herein described may vary in slight detail due to climatic and soil conditions under which the variety may be grown.

The following is claimed:

A new and distinct variety of peach tree as illustrated and described, characterized by its general resemblance in tree and fruit to the parent Redhaven peach, but distinctively characterized by fruit having a ripening period approximately two weeks earlier than said Redhaven peach; and further characterized by a blooming period which averages three to four days earlier.

References Cited in the file of this patent

UNITED STATES PATENTS

Pl. Pt. 1,626 Boos ---------- Aug. 6, 1957